(12) United States Patent
Mahon

(10) Patent No.: US 9,962,286 B2
(45) Date of Patent: May 8, 2018

(54) WOMEN'S UNDERWEAR WITH LABIAL COOLING

(71) Applicant: Theresa R. Mahon, Portchester, NY (US)

(72) Inventor: Theresa R. Mahon, Portchester, NY (US)

( * ) Notice: Subject to any disclaimer, the term of this patent is extended or adjusted under 35 U.S.C. 154(b) by 428 days.

(21) Appl. No.: 14/860,556

(22) Filed: Sep. 21, 2015

(65) Prior Publication Data

US 2017/0079836 A1   Mar. 23, 2017

(51) Int. Cl.
| | | |
|---|---|---|
| *A61F 7/02* | (2006.01) | |
| *A61F 13/84* | (2006.01) | |
| *A61F 7/10* | (2006.01) | |
| *A61F 13/66* | (2006.01) | |
| *A61F 13/72* | (2006.01) | |
| *A61F 13/496* | (2006.01) | |
| *A61F 7/00* | (2006.01) | |
| *A61F 13/15* | (2006.01) | |

(52) U.S. Cl.
CPC .............. *A61F 7/103* (2013.01); *A61F 7/10* (2013.01); *A61F 13/496* (2013.01); *A61F 13/665* (2013.01); *A61F 13/72* (2013.01); *A61F 13/84* (2013.01); *A61F 2007/005* (2013.01); *A61F 2007/026* (2013.01); *A61F 2007/0236* (2013.01); *A61F 2007/0238* (2013.01); *A61F 2007/108* (2013.01); *A61F 2013/1517* (2013.01)

(58) Field of Classification Search
CPC ...... A61F 7/10; A61F 7/103; A61F 2007/005; A61F 2007/0233; A61F 2007/0236; A61F 2007/0238; A61F 2007/108; A61F 13/472; A61F 13/496; A61F 13/66; A61F 13/665; A61F 13/74; A61F 13/76; A61F 13/84; A61F 2013/1517; A61F 2013/47281

See application file for complete search history.

(56) References Cited

U.S. PATENT DOCUMENTS

| | | | | |
|---|---|---|---|---|
| 4,382,443 | A | * | 5/1983 | Shafer ..................... A61F 13/72 |
| | | | | 604/373 |
| 5,167,655 | A | * | 12/1992 | McCoy ..................... A61F 7/10 |
| | | | | 2/406 |
| 5,702,375 | A | * | 12/1997 | Angelillo .................. A61F 7/03 |
| | | | | 602/2 |

(Continued)

*Primary Examiner* — Lynne Anderson
(74) *Attorney, Agent, or Firm* — Brenda Pomerance

(57) ABSTRACT

Panty underwear includes a pouch disposed above the crotch panel and between the leg openings. The pouch has a top opening opposite the wearer's vaginal opening, so that vaginal discharge flows to a sanitary napkin between the bottom of the pouch and the crotch panel. The pouch provides cooling to the wearer's labia and, in some embodiments, to her perineal area. The cooling is provided by either a single generally rectangular cooling pack, or two cooling packs each being rectangular or J-shaped. The sanitary napkin can be internal or external to the pouch. Some embodiments of the underwear are intended for single use. Other embodiments of the underwear are intended to be re-usable, in that the sanitary napkin can be replaced and/or the cooling pack(s) can be re-used. The cooling pack(s) can be sealed with one-time or reusable thermal material therein, or they can be resealable with replaceable thermal material.

14 Claims, 10 Drawing Sheets

(56) References Cited

U.S. PATENT DOCUMENTS

| | | | |
|---|---|---|---|
| 8,937,212 B2* | 1/2015 | Fogg | A61F 7/10 604/291 |
| 2006/0101558 A1* | 5/2006 | Coleman | A41D 13/1254 2/400 |
| 2010/0114053 A1* | 5/2010 | Mandeville | A61F 7/02 604/385.06 |
| 2013/0158635 A1* | 6/2013 | Federico | A61F 7/02 607/108 |
| 2015/0282980 A1* | 10/2015 | Ogunleye | A61F 7/10 607/108 |

* cited by examiner

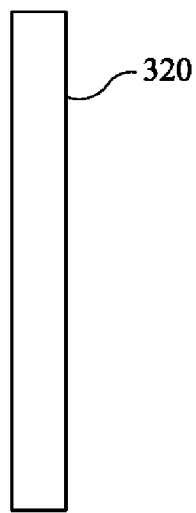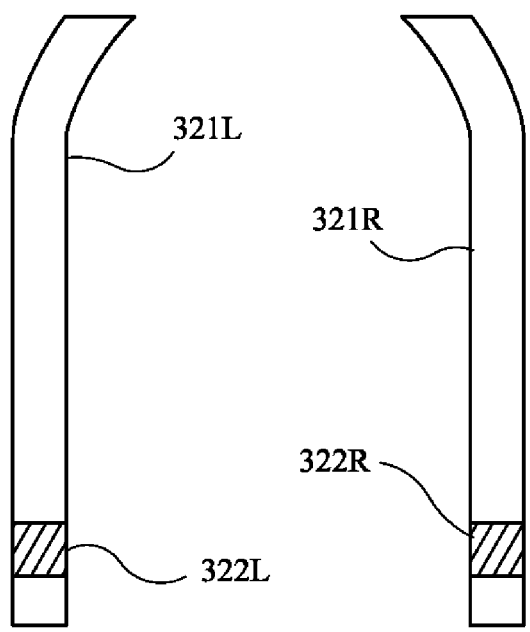
FIG. 4E    FIG. 4F    FIG. 4G

WOMEN'S UNDERWEAR WITH LABIAL COOLING

BACKGROUND OF THE INVENTION

The present invention relates to women's underwear, and more particularly, is directed to underwear for labial cooling.

After vaginal birth, a woman often suffers swollen or edematous labia majora. FIG. 5 is a chart showing female external genital anatomy.

The second stage of labor is when a woman becomes fully dilated and begins the arduous task of pushing and bearing down to deliver her infant vaginally. This process may take several hours. Often, after maternal pushing efforts, the labia can become markedly edematous, which can be very uncomfortable for the mother during the early postpartum period. In addition, it is not uncommon for the mother to sustain lacerations or tears to the vagina, labia, and perineum, as well as periurethral and clitoral areas, during a vaginal delivery. In some cases an episiotomy (surgical incision) is made at the base of the vaginal opening to facilitate delivery of the newborn. These lacerations and/or an episiotomy can also contribute to maternal discomfort in the postpartum period. The discomfort from edematous labia, lacerations and/or episiotomy can be relieved with the application of cold treatment therapy, especially in the immediate postpartum period (first 24 hours).

Vaginal discharge and/or bleeding is also common after giving birth, and may last as long as six weeks.

U.S. Pat. No. 5,167,655 (McCoy) shows a panty having a crotch with a two layer pouch. A sanitary napkin is inserted in the layer of the pouch closest to the body. A cold pack is inserted in the layer of the pouch furthest from the body. The cold pack is distant from the anatomy where it is needed due to the absorbent napkin that sits between the cold pack and the anatomy where the cold pack is needed, thus reducing the benefit of the cold treatment therapy.

U.S. Patent Application Publication No. 2011/0319841 (Romie) recognized the problem with McCoy's two-layer crotch panty, and proposed an ice pack positioned along the center of the crotch, and having a thin sanitary pad along each of the lateral edges of the ice pack. The pad/pack/pad device has an adhesive strip on the side distant from the body, to adhere to a panty. Romie is ill-suited to the majority of postpartum situations where most of the blood emerges from the vaginal opening; Romie locates its sanitary pads to the sides of the vaginal opening rather than directly opposite the wearer's vaginal opening. Additionally, Romie's sanitary pads obstruct therapeutic cooling to the labia, because the pads are next to the labia. U.S. Pat. No. 6,508,794 (Palumbo) shows a disposable device—not a panty—having a urine collecting receptacle. The device has an aperture surrounded by a flange made of hydrophobic material. Absorbent material is contained within the receptacle.

There remains a need for improved panty underwear adapted for post-partum edematous labia, lacerations and/or episiotomy, particularly when combined with vaginal discharge and/or bleeding.

SUMMARY OF THE INVENTION

In accordance with an aspect of this invention, there is provided an undergarment comprising a panty with (a) a hip opening at the top of the panty for enclosing a wearer's hips, (b) left and right leg openings at the bottom of the panty for enclosing the wearer's legs; (c) a crotch panel between the left and right leg openings; and (d) a pouch disposed above the crotch panel and coupled to the crotch panel. The pouch has (i) a central opening opposite the wearer's vaginal opening, and (ii) left and right cooling areas opposite the wearer's left and right labia majora.

A sanitary napkin can be disposed between the central opening of the pouch and the crotch panel. The pouch can be formed of a hydrophobic material, can have a perineal cooling area opposite the wearer's perineal area, and can have cooling material contained between its top surface and bottom surfaces. The cooling material can be removable.

The cooling material can be contained in the pouch itself, or the pouch can contain left and right cooling packs each containing cooling material. The cooling packs can be removable, can be J-shaped, and can be reclosable so that the cooling material can be removed from the cooling packs.

It is not intended that the invention be summarized here in its entirety. Rather, further features, aspects and advantages of the invention are set forth in or are apparent from the following description and drawings.

BRIEF DESCRIPTION OF THE DRAWINGS

FIGS. 4E-4G are top-down views of cooling packs usable with pouch 300;

DETAILED DESCRIPTION

Panty underwear includes a pouch disposed above the crotch and between the leg openings. The pouch has a top opening opposite the wearer's vaginal opening, so that vaginal discharge flows to a sanitary napkin. The pouch provides cooling to the wearer's labia and, in some embodiments, to her perineal area. The cooling is provided by either a single U-shaped cooling pack, or two cooling packs each being rectangular or J-shaped. The sanitary napkin can be internal or external to the pouch.

Some embodiments of the underwear are intended for single use. Other embodiments of the underwear are intended to be re-usable, in that the sanitary napkin can be replaced and/or the cooling pack(s) can be re-used. The cooling pack(s) can be sealed with one-time or reusable thermal material therein, or they can be resealable with replaceable thermal material.

One advantage of the present invention is that cooling is provided directly to the labia majora, where cooling is most needed. The prior art provides cooling to the bottom of a sanitary napkin or to the vaginal orifice, rather than to the labia majora.

Another advantage of the present invention is that conventional sanitary napkins are fully utilized to absorb fluid discharge, and keep the discharge away from the wearer's body.

Another advantage of the present invention is that the wearer's regular underwear is protected from postpartum fluids.

The inventive underwear may be used in a hospital or non-hospital (home) setting. It is simple to configure and use.

Figure 1A:
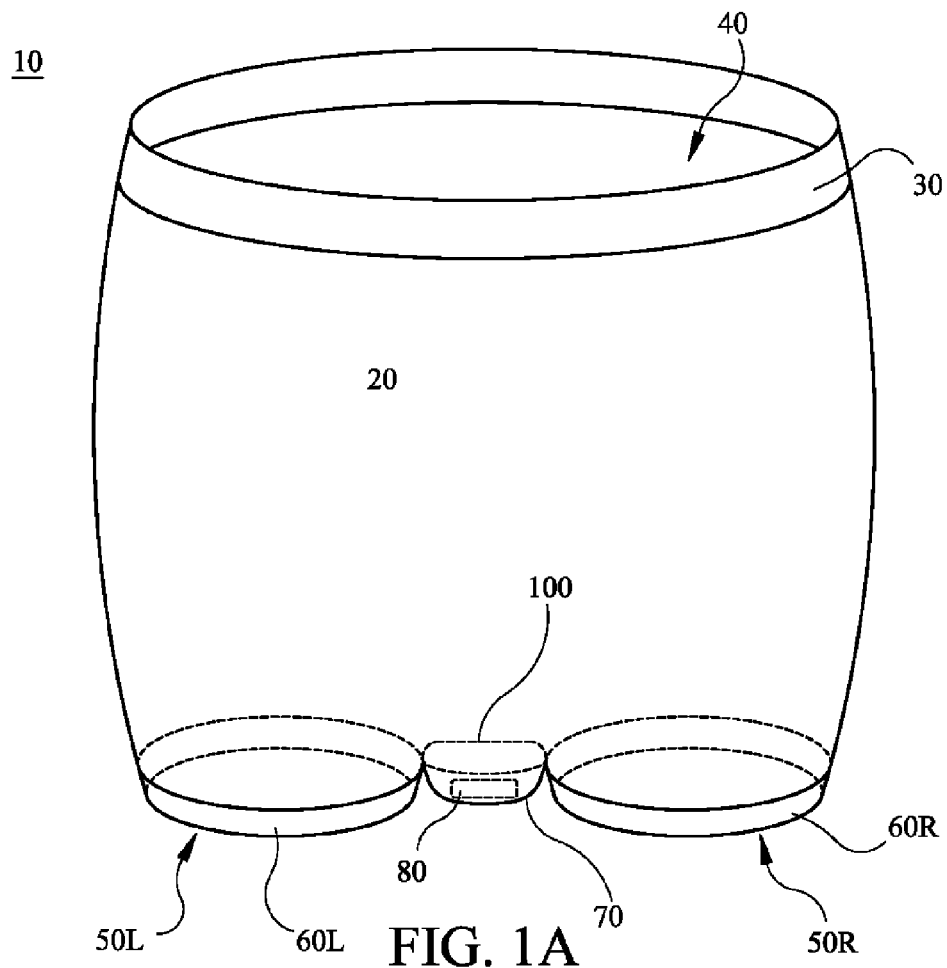
FIG. 1A is a three-dimensional view of panty underwear 10.

FIG. 1A is a three-dimensional view of panty underwear 10. Underwear 10 is made of soft cotton, microfiber, polyester, paper, TYVEK or other suitable material. Underwear 10 has main body 20 having waistband 30, preferably elasticized, forming opening 40 that encircles the waist or hips of a wearer. Underwear 10 has left and right leg openings 50L, 50R formed by leg bands 60L, 60R that are preferably slightly elasticized. Leg bands 60L, 60R have weaker elasticity than waistband 30. Crotch panel 70 is the portion of main body 20 between leg openings 50L, 50R.

Underwear 10 is available in different sizes, such as small, medium, large, and extra-large, to fit women of different sizes and shapes. Main body 20 of underwear 10 may be formed of panels sewn together, or may be created in one piece, such as by tubular knitting.

Underwear 10 may be in the form of a brief panty, a hipster panty, a thong panty, a boyshort panty, or other undergarment. Underwear 10 is shown with closed hips, but in other embodiments, the hip edges may be reclosable, such as by hook and loop fastener, e.g., VELCRO.

Pouch 100 is disposed above crotch panel 70. Sanitary napkin 80 is disposed between pouch 100 and crotch panel 70. In some embodiments, a pouch-shaped area is formed between the bottom of pouch 100 and the top side, i.e., the wearer-facing side, of crotch panel 70.

Figure 1B:
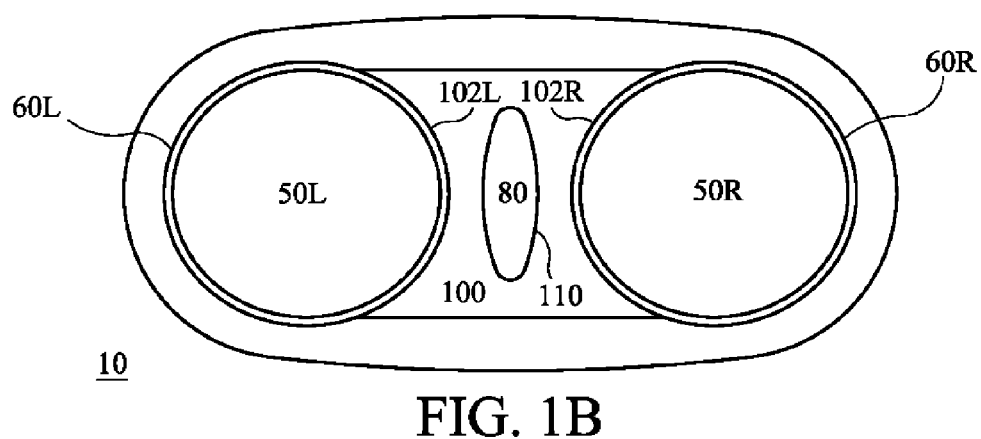
FIG. 1B is a top-down view showing pouch 100 disposed above crotch panel 70 of underwear 10, and sanitary napkin 80 visible through the opening of pouch 100.

FIG. 1B is a top-down view showing pouch 100 disposed above crotch panel 70 of underwear 10. Left and right lateral edges 102L, 102R of pouch 100 are affixed to the lateral edges of crotch panel 70, such as by sewing, fusing or adhesive. Pouch 100 has generally elliptical opening 110 located so as to be opposite the vaginal opening of the wearer. Sanitary napkin 80 is directly below opening 110.

Figure 1C:
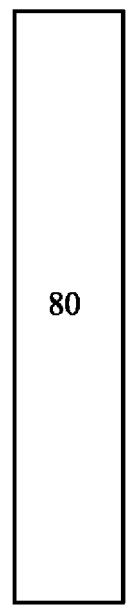
FIG. 1C is a top-down view of sanitary napkin 80.

FIG. 1C is a top-down view of sanitary napkin 80 showing that it has a generally rectangular shape. A conventional sanitary napkin is made of ultra-absorbent material, may have multiple layers, and has a size of approximately 11" length by 3" width by 0.5" thickness.

Figure 1D:
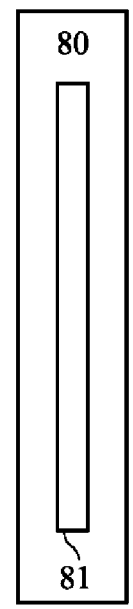
FIG. 1D is a bottom-up view of sanitary napkin 80.

FIG. 1D is a bottom-up view of sanitary napkin 80 showing adhesive strip 81. In some embodiments, a conventional sanitary napkin without an adhesive strip is used. In other embodiments, a conventional maternity napkin without an adhesive strip is used. A maternity napkin is larger than a sanitary napkin.

Figure 2A:
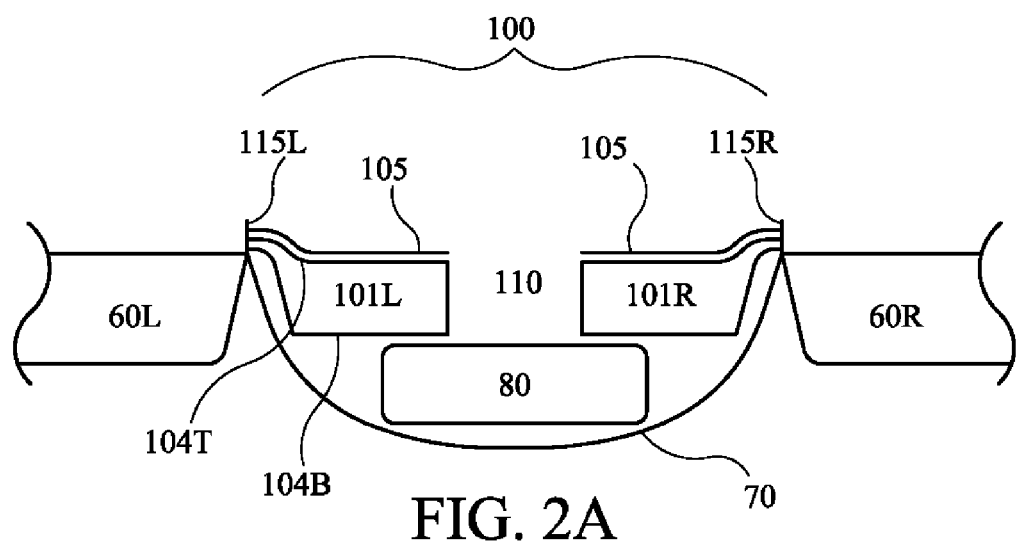
FIG. 2A is a cross-sectional view of pouch 100.

FIG. 2A is a cross-sectional view of pouch 100, midway between the front (nearest to wearer's abdomen) and back (nearest to wearer's derriere) of underwear 10, showing that comfort panel 105 may be disposed above pouch 100. Pouch 100 has a size of approximately 11.5" length by 3.5" width by 0.75" thickness.

Figure 2B:
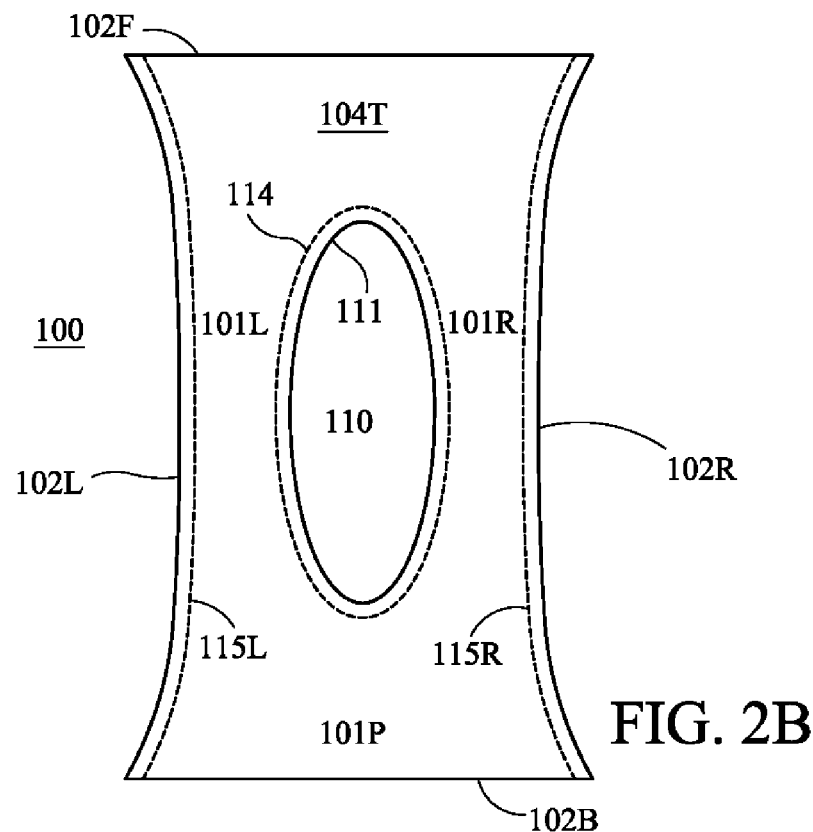
FIGS. 2B and 2C are top-down views of pouch 100.
Figure 2C:
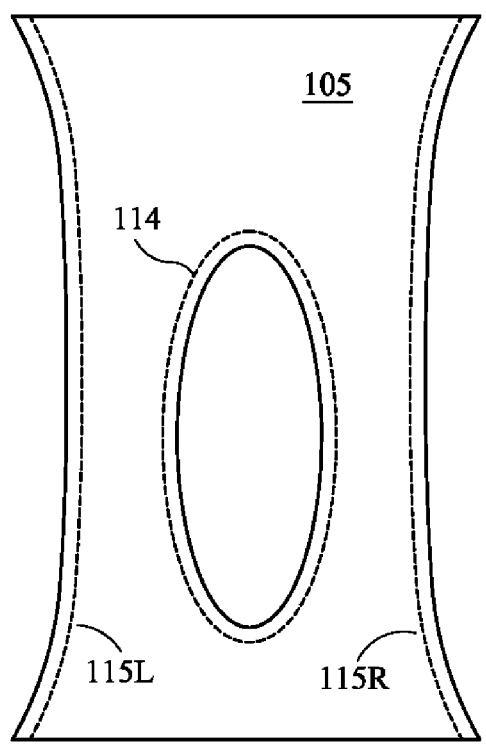
Figure 2D:
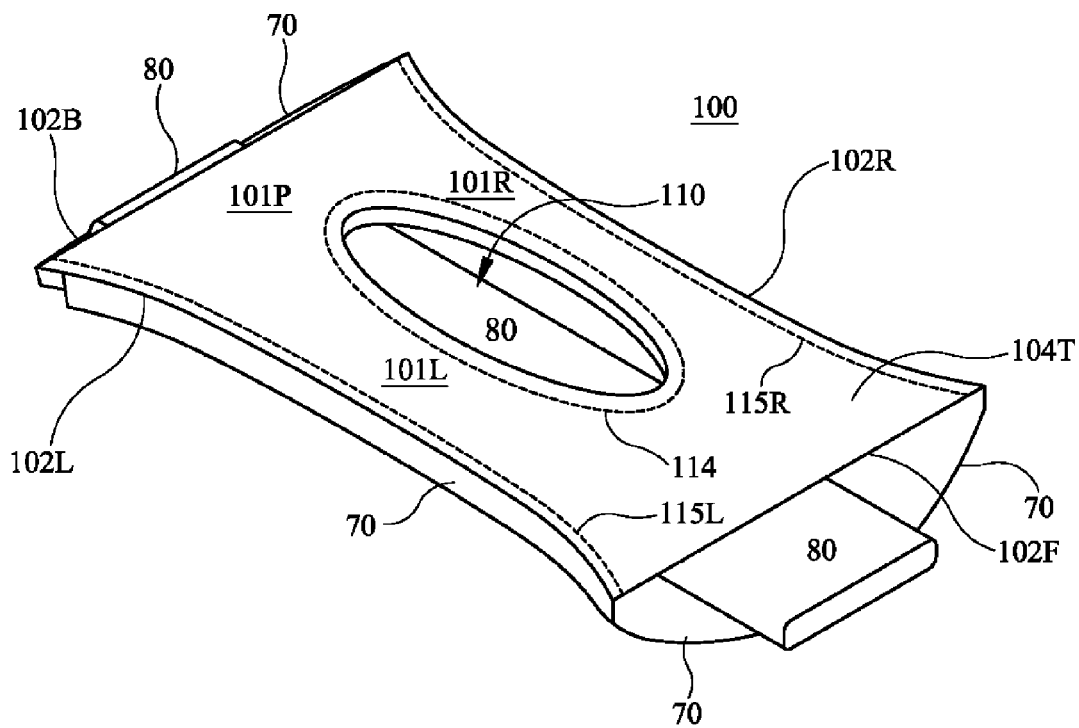
FIG. 2D is a three-dimensional view of pouch 100.

FIGS. 2B and 2C are top-down views of pouch 100; FIG. 2B shows an embodiment without comfort panel 105, while FIG. 2C shows an embodiment with comfort panel 105. Comfort panel 105 is made of a soft absorbent material such as thin felted cotton. FIG. 2D is a three-dimensional view of pouch 100.

Pouch 100 has arc-shaped lateral edges 102L, 102R that generally conform to the shape of the wearer's inner thighs. In some embodiments, edges 102L, 102R are straight edges. Pouch 100 has top surface 104T and bottom surface 104B that are similarly shaped, the top and bottom surfaces are fused or permanently connected along corresponding edges forming a cavity containing a thermal material such as bentonite, glycol or silica gel, or even peas or water, that can be cooled or frozen, and will then slowly return to ambient room temperature, thereby providing cooling. Opening seam 114 permanently connects the edges of opening 110 in the top and bottom surfaces of pouch 100. Left and right lateral seams 115L, 115R permanently respectively connect the left and right lateral edges of top and bottom surfaces of pouch 100.

For some single use embodiments, pouch 100 is filled with ammonium nitrate and water, and is squeezed to begin cooling. Other one-time use thermal materials may be used.

Generally, the top (closest to the wearer) and bottom (furthest from the wearer) surfaces of pouch 100 are formed of the same hydrophobic or waterproof material, such as polyurethane, nylon, plastic, or neoprene. In some embodiments, the top surface is thinner than the bottom surface, to direct cooling to the wearer's body. In some embodiments, the top and bottom surfaces of pouch 100 are formed of different materials. Preferably, the bottom surface of pouch 100 is always strictly waterproof. Comfort panel 105 may be included to shield the wearer's body from chafing against plastic and/or to absorb moisture.

Figure 5:
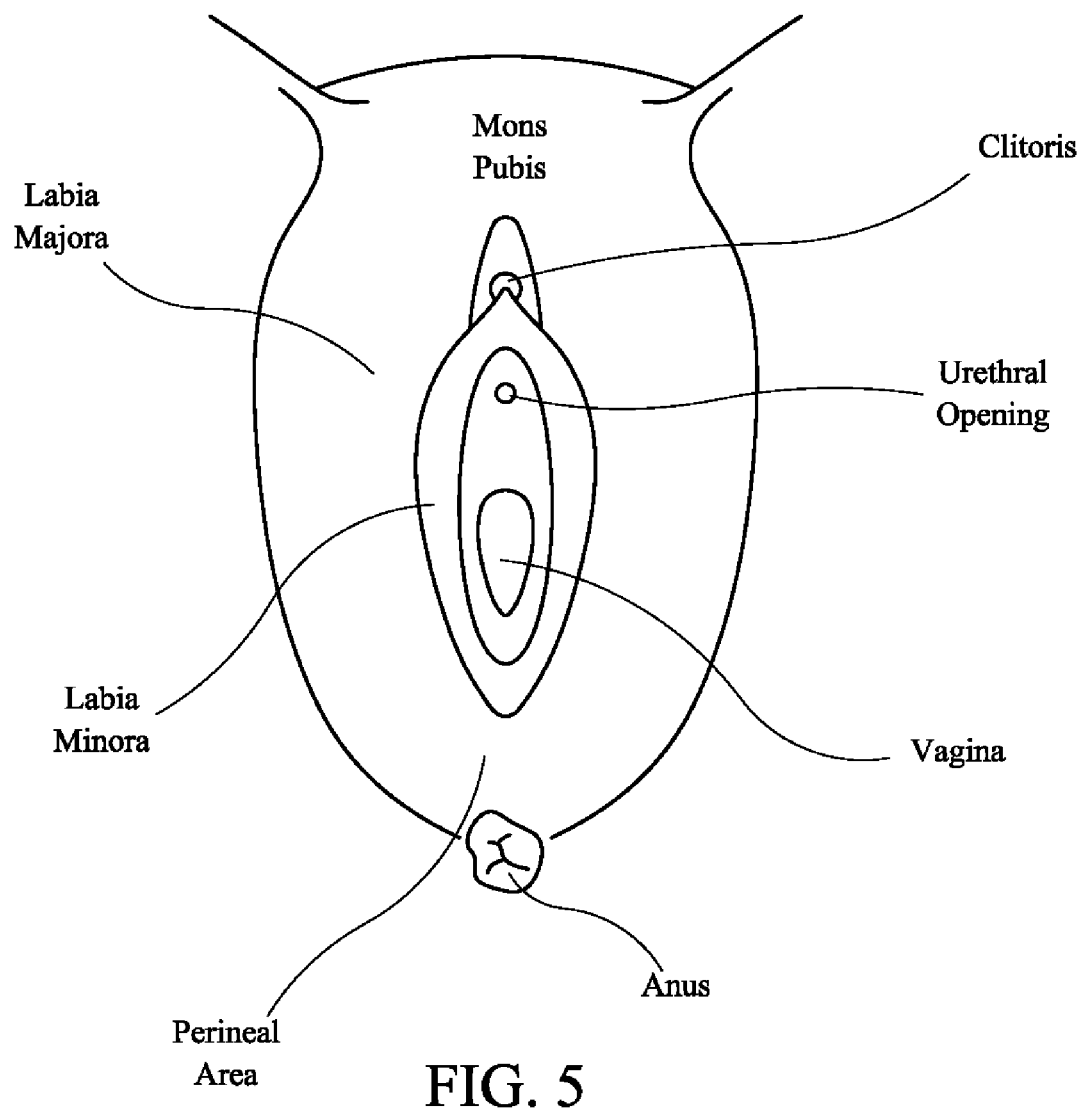
FIG. 5 is a chart showing female external genital anatomy.

Pouch 100 provides left cooling area 101L for the wearer's left labia majora, right cooling area 101R for the wearer's right labia majora, and perineal cooling area 101P for the wearer's perineal area. Areas 101L, 101R and 101P are each portions of top surface 104T of pouch 100. Pouch 100 is generally quadrilateral-shaped with a central opening; the important distinction is between a single pouch that provides cooling to the labia majora and perineal area from one coolant, see FIG. 5, versus a pouch having two separate coolants for each of the left and right labia majora, described below with respect to pouch 300.

In a one-time use version of underwear 10, sanitary napkin 80 is placed between pouch 100 and crotch panel 70, with adhesive strip 81 in contact with crotch panel 70 when adhesive strip 81 is present. Front and back edges 102B, 102F of pouch 100 are left loose; in some embodiments, at least one of front and back edges 102B, 102F is affixed to crotch panel 70, such as by sewing. Underwear 10 is placed in a freezer or refrigerator to cool its thermal material. Or, if the thermal material is ammonium nitrate or other single-use material, no advance cooling is needed.

If comfort panel 105 is present, it is usually sewn along its outer lateral edges to the outer lateral edges of the top surface of pouch 100.

When the wearer is ready to use underwear 10, it is removed from the freezer or refrigerator, or, if the thermal material is ammonium nitrate, pouch 100 is squeezed to begin cooling.

In use, the wearer puts her legs through leg openings 50L, 50R and positions waistband 30 around her waist or hips. The labia majora and perineal area of the wearer are cooled by pouch 100. Fluid may flow from the wearer's vaginal opening to sanitary napkin 80. Pouch 100 helps keep sanitary napkin 80 from slipping, while sanitary napkin 80 helps keep pouch 100 positioned against the labia and perineum of the wearer.

When sanitary napkin 80 is substantially full, underwear 10 is disposed of.

In addition to or instead of the filling of the sanitary napkin, return of the thermal material to ambient room temperature may be the trigger for disposing of underwear 10.

In a re-usable version of underwear 10, at least one of front and back edges 102B, 102F remains unaffixed to crotch panel 70, so that a sanitary napkin can be removed and another sanitary napkin inserted. Underwear 10 is placed in a freezer or refrigerator to cool its thermal material. When the wearer is ready to use underwear 10, it is removed from the freezer or refrigerator, and sanitary napkin 80 is inserted between the top (wearer facing) side of crotch panel 70 and the bottom of pouch 100 through the unaffixed one of front and back edges 102B, 102F; adhesive strip 81 is not activated.

If comfort panel 105 is present, it is usually attached along its bottom side (away from wearer) to the top surface of pouch 100 using removable adhesive.

In use, the wearer puts her legs through leg openings 50L, 50R and positions waistband 30 around her waist or hips. The labia majora and perineal area of the wearer are cooled by pouch 100. Fluid may flow from the wearer's vaginal opening to sanitary napkin 80. When sanitary napkin 80 is full, underwear 10 is removed.

Underwear 10 is prepared for re-use by pulling the used sanitary napkin through the unaffixed one of edges 102B, 102F of pouch 100. The top (wearer facing) side of pouch 100 is wiped clean, and/or the used comfort panel is removed and a fresh comfort panel applied. A fresh sanitary napkin is inserted through the unaffixed edge of pouch 100. Generally, between removing a used sanitary napkin and inserting a fresh sanitary napkin, underwear 10 is cooled or frozen again. Thus, it is helpful for the wearer to have at least two pairs of underwear 10, so that one pair can be cooling while the other pair is being worn.

A reusable version of underwear 10 can simply be discarded after one use. That is, because underwear 10 is capable of re-use does not mean it is required to be re-used.

Figure 3A:
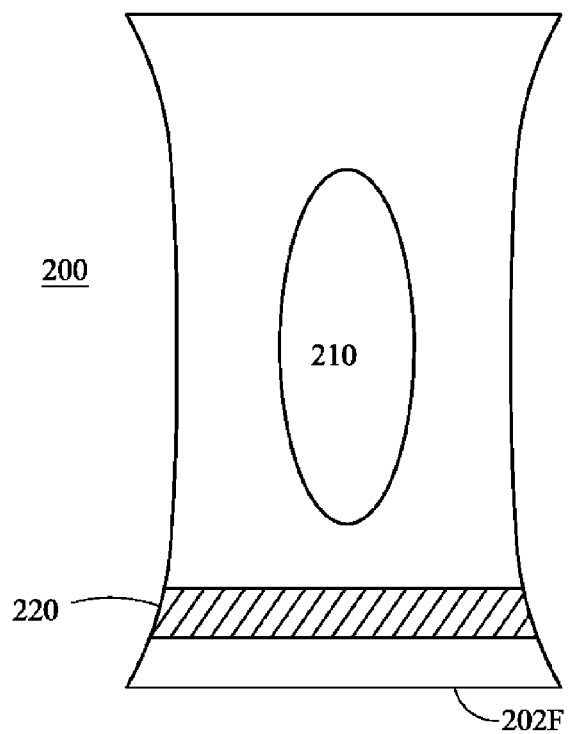
FIG. 3A is a top-down view of pouch 200.
Figure 3B:
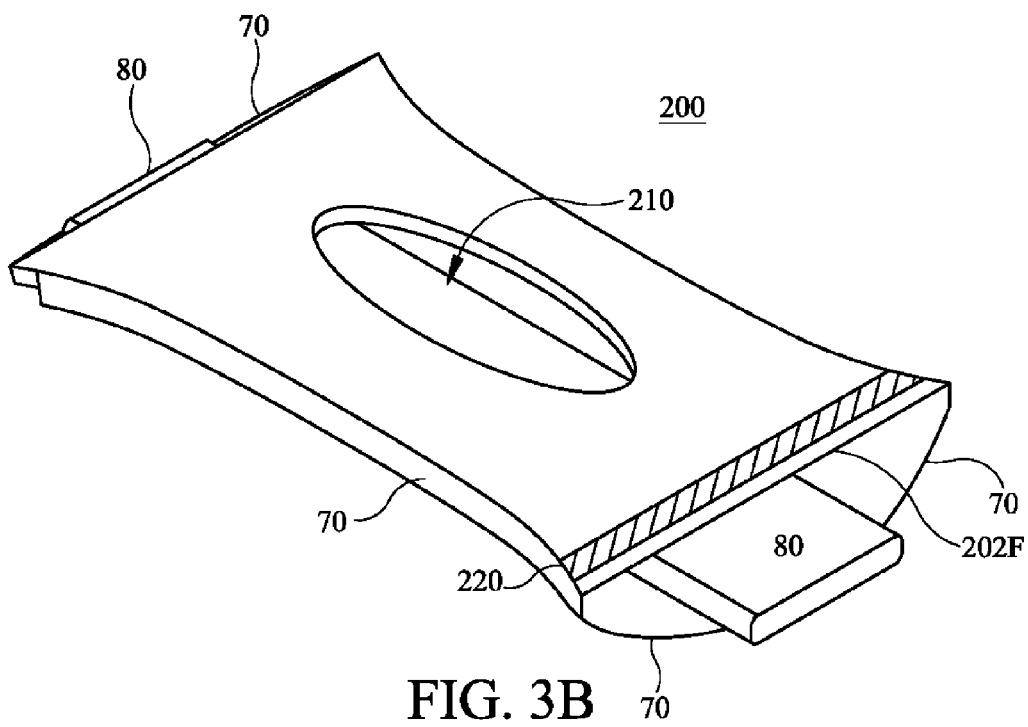
FIG. 3B is a three-dimensional view of pouch 200.

FIG. 3A is a top-down view of pouch 200. Pouch 200 is substituted for pouch 100 in some re-usable embodiments of underwear 10. Pouch 200 is generally similar to pouch 100, except as discussed. Pouch 200 has reclosable seam 220, such as a ZIP-LOC seam, parallel to front edge 202F. FIG. 3B is a three-dimensional view of pouch 200.

Prior to using underwear 10, reclosable seam 220 is opened, pouch 200 is filled with thermal material, such as water, ice chips or frozen peas, reclosable seam 220 is closed, and underwear 10 is placed in a freezer or refrigerator. When the wearer is ready to use underwear 10, it is removed from the freezer or refrigerator, and sanitary napkin 80 is inserted as above.

Pouch 200 is used and re-used as above, except that between removing a used sanitary napkin and inserting a fresh sanitary napkin, the old thermal material may be discarded by opening reclosable seam 220 and evacuating the old thermal material, and then new thermal material is inserted and reclosable seam 220 is closed.

Embodiments having multiple cooling packs will now be discussed.

Pouch 300 is substituted for pouch 100 in some embodiments. Pouch 300 is similar to pouch 100, except as discussed below.

Figure 4A:
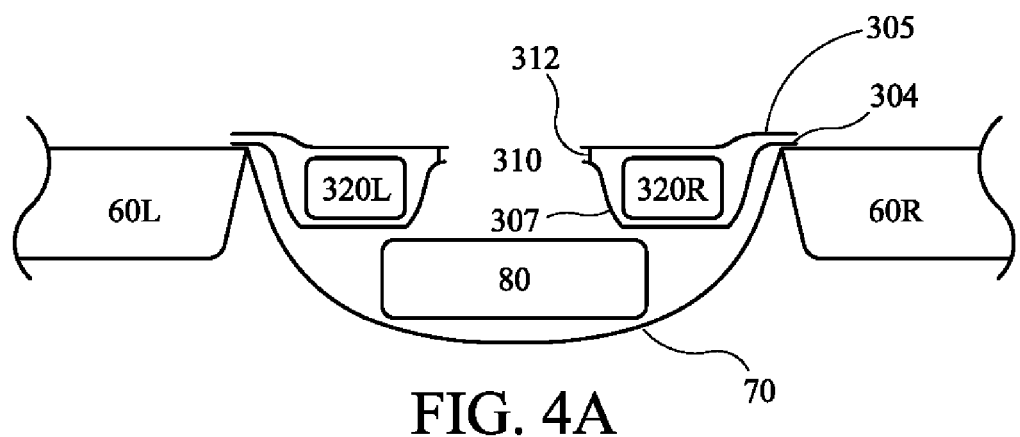
FIGS. 4A and 4B are cross-sectional views of pouch 300.
Figure 4B:
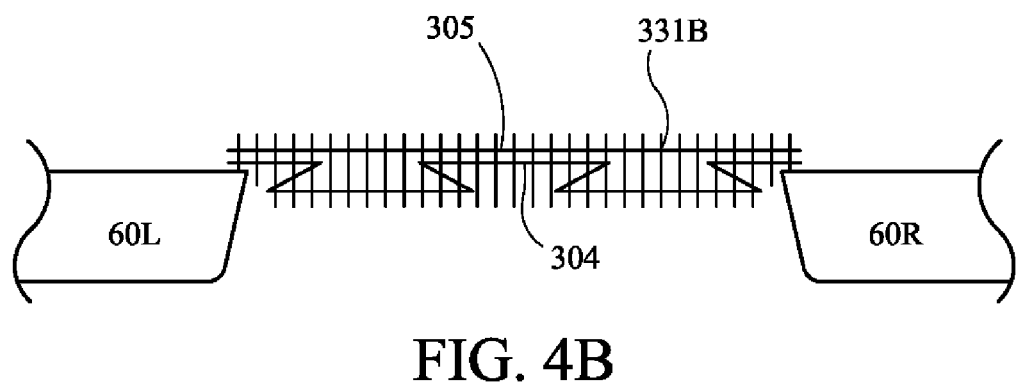
Figure 4C:
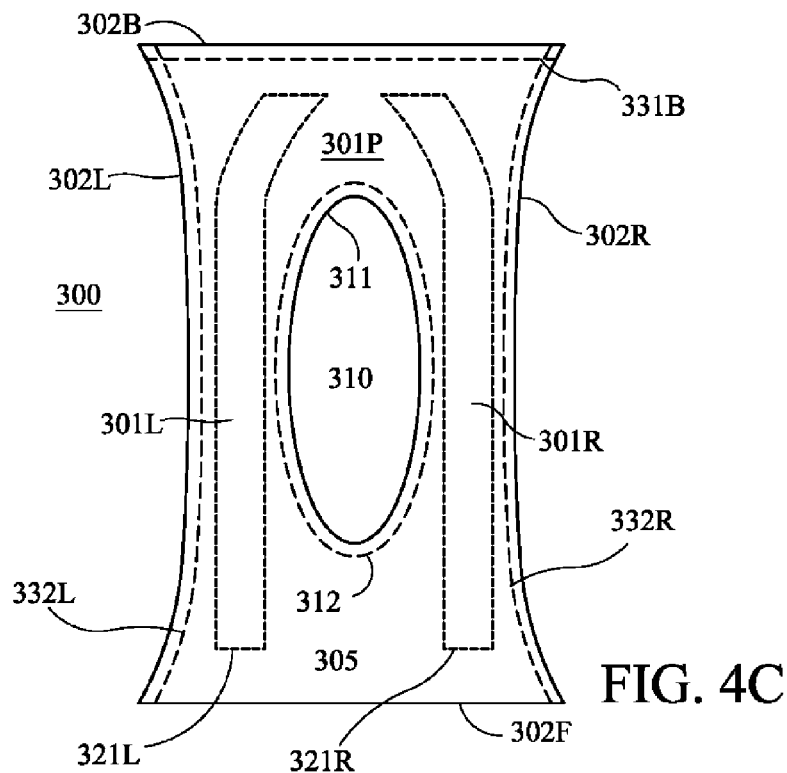
FIG. 4C is a top-down view of pouch 300.

FIG. 4A is a cross-sectional view of pouch 300, midway between the front (nearest to wearer's abdomen) and back (nearest to wearer's derriere) of underwear 10. FIG. 4B is a cross-section view of pouch 300 at the back of underwear 10. FIG. 4C is a top-down view of pouch 300 showing top piece 305, also referred to as top surface 305.

Pouch 300 has top surface 305 formed of a lightweight, comfortable, waterproof and water repellant material that avoids chafing against the wearer's skin, such as polyurethane, nylon, plastic, neoprene, treated cotton, treated microfiber or treated polyester.

Pouch 300 has bottom surface 304 formed of a hydrophobic or waterproof material such as polyurethane, nylon, plastic, or neoprene. Bottom surface 304 is usually a thicker material than top surface 305.

In some embodiments, top surface 305 and bottom surface 304 have the same shape. In other embodiments, top surface 305 and bottom surface 304 have different shapes, because bottom surface is larger to form compartments for cooling packs.

Figure 4D:
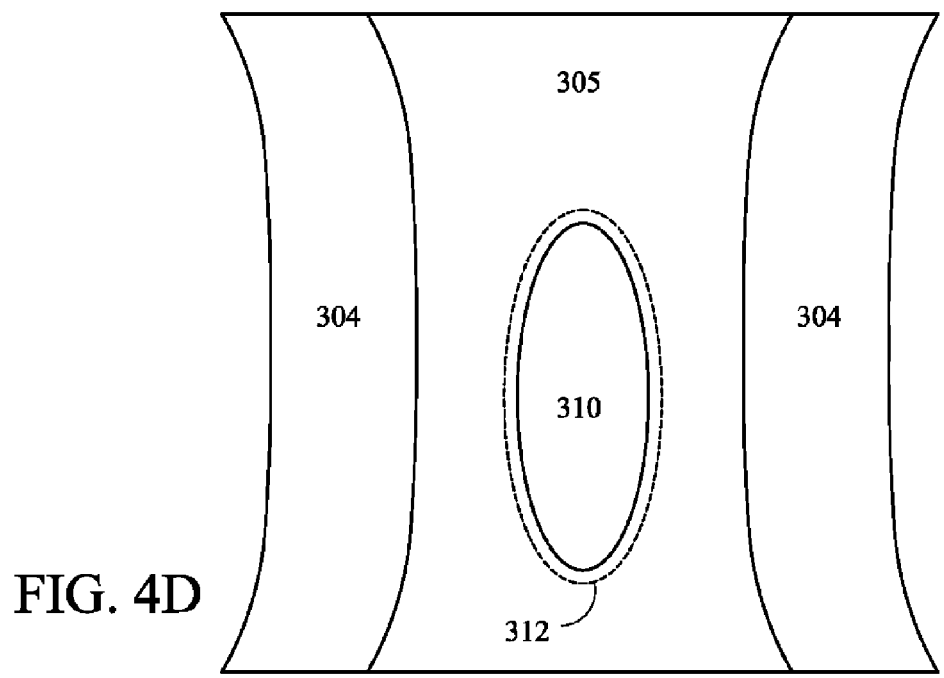
FIG. 4D shows partially assembled top surface 305 and bottom surface 304 of pouch 300.

FIG. 4D shows partially assembled top surface 305 and bottom surface 304 of pouch 300. Flat top piece 305 is laid atop flat bottom piece 304 so that the central openings align, and the edges of the central openings are fused or sewn together along seam 312.

The front and back edges of bottom piece 304 are accordion-folded as shown in FIG. 4B, or gathered. In some embodiments, the front and back edges of top piece 305 are temporarily stretched to match the corresponding edges of bottom piece 304. Then, the back edges of top piece 305 and bottom piece 304 are fused or sewn together along back seam 331B. In some embodiments, after cooling packs (discussed below) are inserted between top surface 305 and bottom surface 304, the front edges of top piece 305 and bottom piece 304 are fused or sewn together.

The arc-shaped left and right lateral edges of top piece 305 and bottom piece 304 are aligned, and permanently attached to the outer edges of crotch panel 70 by sewing, fusing or other suitable technique along seams 332L, 332R. As shown in FIG. 4C, pouch 300 has left labia cooling area 301L, right labia cooling area 301R and perineal cooling area 301P. FIG. 4A shows generally upright inner wall 307 of a compartment formed by folding bottom piece 304 as described above.

Figure 4H:
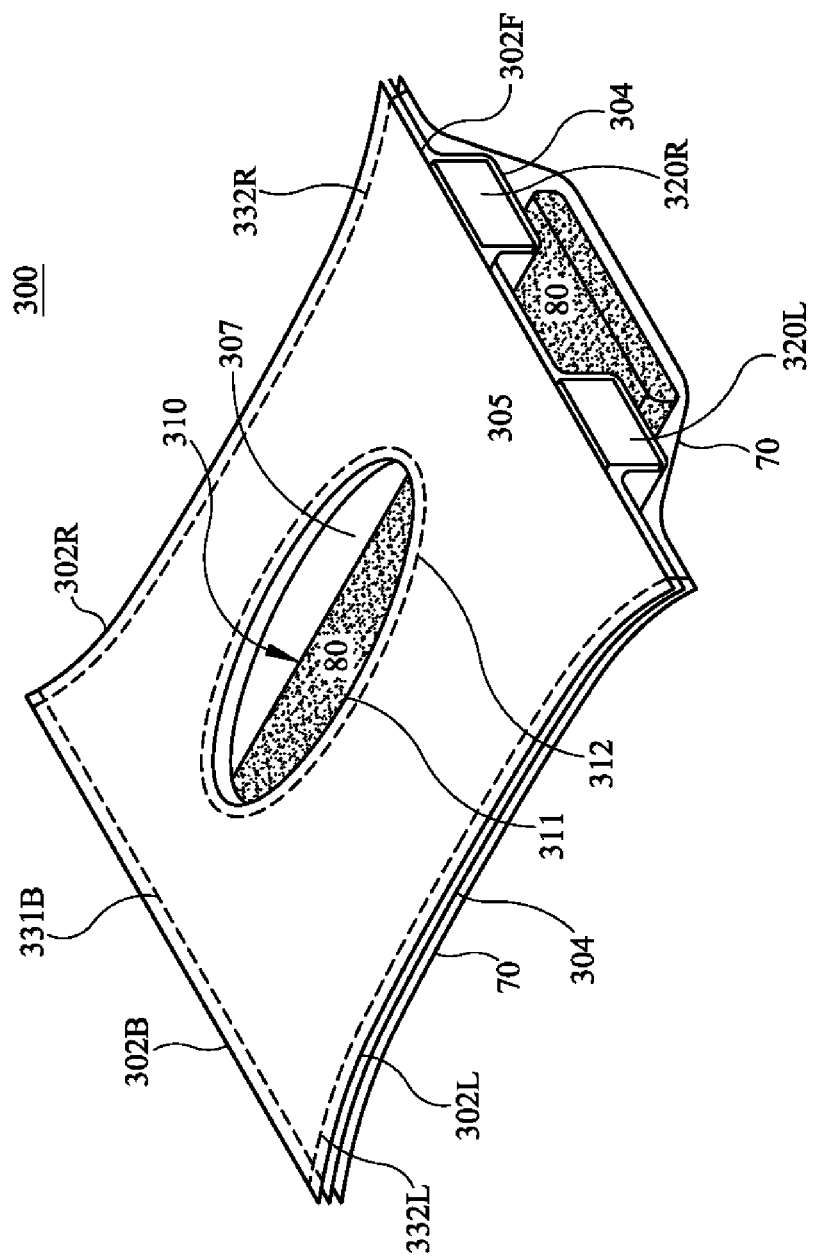
FIG. 4H is a three-dimensional view of pouch 300.

FIGS. 4E-4G are top-down views of cooling packs usable with pouch 300. FIG. 4H is a three-dimensional view of pouch 300. Cooling pack 320 has a rectangular shape and a size of about 5" length by 0.75" width by 0.75" thickness; two instances of cooling pack 320 are used for pouch 300: one for the left side and one for the right side. Cooling pack 320 is formed of a strictly waterproof material such as plastic or polyurethane. Cooling pack 320 is filled with a thermal material as discussed above. Cooling pack 320 functions to cool a respective one of the labia majora of the wearer of underwear 10.

Cooling packs 321L and 321R are similar to cooling pack 320, except that they are each J-shaped, and have a size of about 6.5" length by 0.75" width by 0.75" thickness. Cooling packs 321L, 321R respectively have reclosable seam 322L, 322R, such as a ZIP-LOC seam, parallel to their front edge. In some embodiments, cooling packs 321L, 321R are permanently sealed. Cooling packs 321L, 321R function to cool the labia majora and the perineal area of the wearer of underwear 10. Cooling packs 321L, 321R are each filled and emptied as described above for pouch 200.

In some embodiments, pouch 300 has left and right cooling packs permanently enclosed therein by permanently connecting the front edges of top piece 305 and bottom piece 304. In other embodiments, the front edges of top piece 305 and bottom piece 304 are left loose, so that the cooling packs can be slipped in and out of pouch 300. FIG. 4C shows, via dotted lines, cooling packs 321L, 321R inserted in pouch 300.

Removable cooling packs advantageously reduce the amount of freezer or refrigerator space needed, as only the cooling packs need be cooled, not the entire underwear 10 garment.

In single use embodiments, sanitary napkin 80 is placed between bottom surface 304 and crotch panel 70, then the lateral edges of pouch 300, that are adjacent to the wearer's inner thighs, are permanently coupled to crotch panel 70.

In some embodiments, instead of one left cooling pack and one right cooling pack, two or more left cooling packs and/or two or more right cooling packs may be used. The cooling packs on each side may be of similar size to the single cooling pack described above and arranged in parallel, or they may be of smaller size and arranged in a row or matrix.

In reusable embodiments, when the wearer is ready to use underwear 10, sanitary napkin 80 is inserted between bottom piece 304 and crotch panel 70.

Underwear 10 having pouch 300 is used and disposed of as generally described above with regard to pouches 100, 200.

Although illustrative embodiments of the present invention, and various modifications thereof, have been described in detail herein with reference to the accompanying drawings, it is to be understood that the invention is not limited to these precise embodiments and the described modifications, and that various changes and further modifications may be effected therein by one skilled in the art without departing from the scope or spirit of the invention as defined in the appended claims.

What is claimed is:

1. An undergarment comprising:
   a panty having:
   (a) a hip opening at the top of the panty for enclosing a wearer's hips;
   (b) left and right leg openings at the bottom of the panty for enclosing the wearer's legs;
   (c) a crotch panel between the left and right leg openings; and
   (d) a pouch disposed above the crotch panel and coupled to the crotch panel, the pouch having:
   (i) a central opening opposite the wearer's vaginal opening, and
   (ii) left and right cooling areas opposite the wearer's left and right labia majora.

2. The undergarment of claim 1, wherein a sanitary napkin is disposed between the central opening of the pouch and the crotch panel.

3. The undergarment of claim 1, wherein the pouch is formed of a hydrophobic material.

4. The undergarment of claim 1, wherein the pouch also has a perineal cooling area opposite the wearer's perineal area.

5. The undergarment of claim 1, wherein the pouch also has a top surface, a bottom surface and cooling material contained between the top surface and the bottom surface.

6. The undergarment of claim 5, wherein an edge of the top surface is reclosably coupled to an edge of the bottom surface, so that the cooling material can be removed from the pouch.

7. The undergarment of claim 5, wherein corresponding edges of the top and bottom surfaces are permanently sealed to each other.

8. The undergarment of claim 1, further comprising a comfort panel located above the pouch, the comfort panel having a central opening aligned with the central opening of the pouch.

9. The undergarment of claim 1, wherein the pouch also has a top surface, a bottom surface, and left and right cooling packs contained between the top surface and the bottom surface, each of the left and right cooling packs containing cooling material.

10. The undergarment of claim 9, wherein the left and right cooling packs are removable.

11. The undergarment of claim 9, wherein the left and right cooling packs are J-shaped.

12. The undergarment of claim 9, wherein the left and right cooling packs are reclosable so that the cooling material can be removed from the cooling packs.

13. The undergarment of claim 9, wherein the left and right cooling packs are permanently sealed so that the cooling material stays in the cooling packs.

14. The undergarment of claim 1, wherein the pouch has arc-shaped lateral edges for conforming to inner thighs of the wearer.

* * * * *